United States Patent [19]

Boss et al.

[11] Patent Number: 5,411,883
[45] Date of Patent: May 2, 1995

[54] PROLIFERATED NEURON PROGENITOR CELL PRODUCT AND PROCESS

[75] Inventors: Barbara D. Boss, Alameda; Dennis H. Spector, Oakland, both of Calif.

[73] Assignee: Somatix Therapy Corporation, Alameda, Calif.

[21] Appl. No.: 928,676

[22] Filed: Aug. 12, 1992

Related U.S. Application Data

[63] Continuation of Ser. No. 631,617, Dec. 21, 1990, abandoned, which is a continuation-in-part of Ser. No. 456,757, Dec. 26, 1989, abandoned.

[51] Int. Cl.$^6$ .............................................. C12N 5/00
[52] U.S. Cl. .............................. 435/240.2; 435/240.1; 435/240.21
[58] Field of Search .............. 435/240.1, 240.2, 240.21

[56] References Cited

PUBLICATIONS

Asou et al, *Brain Research* 332:355–357 (1985).
Barakat et al, *Neurochem. Research* 7(3):287–300 (1982).
Brundin et al, *Neurosci. Letters* 61:79–84 (1985).
Buse et al, *Int. J. Devel. Neuroscience* 7:103–113 (1989).
Doering et al, *Dev. Brain Res.* 5:229–233 (1982).
Frederiksen et al, *Soc. Neurosci. Abstr.* 12:1122 (1986).
Honegger et al, *Nature* 282:305–307 (1979).
Kamo et al, *Brain Res.* 397:372–376 (1986).
Kriegstein et al, *Brain Research* 295:184–189 (1984).
Temple, *Nature* 340:471–473 (1989).
Wu et al., *J. Cell. Physiol.* 136:367–372 (1988).
Yoshida et al, *Neurosci. Letters* 70:34–39 (1986).

Boss et al., *Soc. Neurosci, Abst.* 15(2):1354 (1989).
Strecker et al., *Exp. Brain Res.*, 76:315–322 (1989).
Huffaker et al., *Exp. Brain Res.* 77:329–336 (1989).
Calof et al. (a), *Neuron* 3:115–127 (1989).
Calof et al. (6), *J. Cell Biol.*, 107 (6 Part 3):510A (1988).
Asou et al., *Brain Research*, 332:355–357 (1985).
Barakat et al, *Neurochem. Research*, 793:287–300 (1982).
Brundin et al, *Neurosci. Letters*, 61:79–84 (1985).

*Primary Examiner*—Jasemine C. Chambers
*Attorney, Agent, or Firm*—Skjerven, Morrill, MacPherson, Franklin & Friel; Laura Terlizzi

[57] ABSTRACT

This invention is based on the development of procedures for isolation and proliferation of neuron progenitor cells and is directed to growth, storage, production and implantation of proliferated neuron progenitor cells. The isolation and culture methods are designed to proliferate mammalian ventral mesencephalon neuron progenitor cells in vitro to produce a culture which differentiates to produce dopamine-producing cells. The products of this invention include a culture containing neuron progenitor cells, preferably, grown as aggregates in suspension cultures. The process of this invention for preparing neuron progenitor cells comprises obtaining ventral mesencephalon tissue from a donor at the appropriate stage of embryonic development; dissociation of the tissue to obtain single cells and small cell clusters for culture; culturing the neuron progenitor cells in an initial culture medium which selects for a novel cell culture containing neuron progenitor cells and growing the cells for a period of time in a second medium, during which the neuron progenitor cells proliferate.

16 Claims, No Drawings

PROLIFERATED NEURON PROGENITOR CELL PRODUCT AND PROCESS

CROSS REFERENCE TO RELATED APPLICATION

This application is a continuation of application Ser. No. 07/631,617, filed Dec. 21, 1990 , now abandoned, which is a continuation-in-part of Ser. No. 07/456,767, filed on Dec. 26, 1989, now abandoned.

FIELD OF THE INVENTION

This invention relates to preparation of proliferated neuron progenitor cells and their implantation. In particular, this invention relates to processes for producing proliferated neuron progenitor cells which can be induced in vivo or in vitro to develop into functional neurons which produce dopamine.

BACKGROUND OF THE INVENTION

The nervous system contains two classes of cells: the nerve cells (or neurons) and neuroglia cells (or glia). These cells are distinguished by morphological, biochemical and functional differences. Morphologically, neurons have a cell body and projecting extensions or neurites (processes) of varying length. In vivo, neuritic extensions are further divided into axons (which transfer signals away from the neuron) and dendrites (which transfer signals to the neuron). Among many other biochemical and biophysical processes, neurons synthesize specific chemicals involved in signaling of information. In the central nervous system (CNS) glia are nine times more prevalent than nerve cells. Glia are thought to serve as neural supportive elements by providing nutrients, growth or survival factors and extracellular matrices. These cells are morphologically distinct from nerve cells and do not synthesize neurotransmitters.

To date, attempts to implant functional neuronal cells have largely been unsuccessful. Once the cells send out neurites in vivo, they are very difficult to transplant. The neurites become damaged during preparation of the implantation culture, leading to the death of the cells. In response to this problem, cells for implantation have been obtained from embryos at a point in the embryonic maturation process prior to neurite formation to eliminate cell death due to disruption of the neurites.

However, it is also undesirable to transplant fresh tissue. A period of time to evaluate the tissue prior to implantation, such as to determine whether the tissue is contaminated with a virus, is highly desirable. To hold the tissue for a period of time, the tissue must either be cultured in vitro or frozen. Fresh tissue is fragile, and does not respond well to freezing. The percentage of viable cells in the fresh tissue is greatly diminished by the freeze/thaw process so that a substantial percentage of the cells in the implant are nonviable. In response to the problems inherent in using fresh or fresh-frozen tissue, attempts to culture undifferentiated cells in vitro for implantation have been performed.

Since the initial discovery 80 years ago by Ross Harrison that nerve fibers can survive under tissue culture conditions, the literature has become inundated with reports using cultured nervous tissue. Neuronal cells in vitro also send out neurites, leading to the same problems of cell death upon disruption of the neurites as encountered with fresh tissue. Therefore, attempts to transplant cells prior to production of the neurites in vitro have been made.

The consensus in the reports regarding dissociated CNS tissue (single cell suspension) is that (1) tissue derived from CNS areas which are no longer displaying neuronal division in vivo will only support glial survival in vitro (see, for example, Hansson et al., Brain Research 300:9–18 [1984]) and (2) tissue derived from CNS areas still undergoing neuronal division in vivo will allow both neuronal and glial survival in vitro; those neurons will not proliferate, but can differentiate to varying degrees under in vitro conditions (see for example, Ahnert-Hilger et al., Neuroscience 17(1):157–165 [1986] and Boss et al., Dev. Brain Res., 36:199–218 [1987]).

Methods which produce cell cultures in vitro in which neuronal cells proliferate are being sought. The method should also minimize the cell loss due to disruption of neurites upon preparation of the cells for implantation. In particular, such cell cultures which would produce dopamine following implantation are highly desirable.

DESCRIPTION OF THE PRIOR ART

A few reports have claimed that a small proportion (6–15%) of neuroblasts obtained from embryonic chick or rat cerebral hemispheres can proliferate under in vitro conditions (see Barakat et al., Neurochem. Research 7(3):287–300 [1982]; Kriegstein et al., Brain Research 295:184–189 [1984]; Asou et al., Brain Research 332:355–357 [1985]; Yoshida et al., Neurosci. Letters 70:34–39 [1986]). Temple, Nature 340:471–473 (1989) reports that individual CNS blast cells isolated from 13.5 to 14.5 day rat forebrain septal region and cultured as single cells in the presence of conditioning cells can divide and differentiate into neuronal cells, glial cells or both.

Buse et al., Int. J. Devel. Neuroscience 7:103–113 (1989) report that in cultures of ventricular cells from the rostral part of the mouse neural plates, ventricular cells developing into neuronal phenotypes immediately stopped proliferating upon transfer to cell culture, while a small portion of cells continued to proliferate, displaying morphological characteristics of radial glial cells. The authors conclude that two types of progenitor cells, committed to either neuronal or glial lineages, coexist in cultured neural plate cells.

Others (Honegger et al., Nature 282:305–307 [1979]), using reaggregates of dissociated fetal rat brain cells, have demonstrated proliferation (but not specifically neuroblast proliferation) as well as differentiation under the same serum-free conditions. Still other workers (Frederiksen et al., Soc. Neurosci. Abstr. 12:1122 [1986]), unable to find significant proliferation in vitro of isolated rat progenitor cells, have turned to genetic manipulation of the cells (using retroviral insertion of oncogenes) to study early developmental events in the CNS.

In a recent article, Wes et al., J. Cell. Physiol. 36:367–372 (1988) stated that there is a general consensus that neuroblasts from embryonic rat brains do not divide in culture, despite reports that contradict this belief.

Regarding transplantation of progenitor cells, Doering et al., Dev. Brain Res. 5:229–233 (1982) have cultured subventricular epithelial cells from the embryonic mouse neopallium (dorsal cerebral cortex or neocortex) without showing any evidence of proliferation and transplanted these cells into the cerebella of neonatal mice. The transplanted developing cerebral cortical cells differentiated into their normal phenotypes in vivo, even though misplaced in the cerebellum, but failed to differentiate properly under in vitro conditions.

Cultured embryonic cells have also been used as transplants intended to alter the unusual turning behavior demonstrated by rats injected unilaterally with 6-hydroxydopamine (6-OHDA) (one of the animal models for Parkinson's disease). Brundin et al., Neurosci. Letters 16:79-84 (1985) used dissociated rat ventral mesencephalon cells cultured for six days and transported for two days for their striatal transplants. They reported that two out of five transplanted animals showed behavioral recovery, with only 1 in 1000 of the cultured cells surviving as tyrosine-hydroxylase (TH)-positive neurons in the grafts after seven weeks in vivo. No claims were made by the authors that the cells in culture had proliferated to any significant extent.

Kamo et al. Brain Res. 397:372-376 (1986), also making no claims regarding proliferation, cultured explants of fetal human paravertebral sympathetic ganglion chains for three weeks to three months prior to using them as aggregates of 1000-4000 neurons for transplantation in their 6-OHDA rat model. Four out of the six transplanted rats showed behavioral recovery as well as surviving TH-positive neurons in the graft (no quantitation reported). Although no immunosuppression was used in these experiments, five out of six grafts, analyzed after 4.5 to 6.0 months, contained surviving TH-positive neurons.

SUMMARY OF THE INVENTION

This invention is based on the development of procedures for isolation and proliferation of neuron progenitor cells and is directed to growth, storage, production and implantation of proliferated neuron progenitor cells. The isolation and culture methods are designed to proliferate neuron progenitor cells in vitro to produce a culture which differentiates to produce dopamine-producing cells. Depending on the culture period and conditions, the progenitor cells differentiate either in vitro or in vivo, following implantation. In addition to increasing the number of neuronal cells, the cultures can be frozen while substantially maintaining cell viability. When cultured as aggregates, the progenitor cell cultures send out neurites which are contained within the aggregates and therefore are not disrupted in the implantation process. Thus, a high percentage of viable cells is maintained.

A portion of the neuron progenitor cells spontaneously differentiate in vitro. Following implantation, a subpopulation of the neuron progenitor cells which did not differentiate in vitro differentiate in vivo and function as tyrosine hydroxylase-containing neurons, gaining the ability to produce functional effects by about three to six months following implantation, depending on the species of donor and host tissue. Alternatively, the neuron progenitor cells can be induced to differentiate in vitro, producing a population of mature neurons which produce dopamine.

The products of this invention include a culture containing neuron progenitor cells. The culture can be progenitor cells or aggregates of progenitor cells in a culture medium, or single or aggregated neuron progenitor cells on or dispersed in a substrate matrix. Most preferably, the cultures are suspension cultures in which the progenitor cells grow as aggregates.

The process of this invention for preparing neuron progenitor cells comprises obtaining ventral mesencephalon tissue from a mammalian donor at the appropriate stage of embryonic development; dissociation of the tissue to obtain single cells and small cell clusters for culture; culturing the neuron progenitor cells in an initial culture medium which selects for a novel cell culture containing neuron progenitor cells (adaptive period) and growing the cells for a period of time (growth period) in a second medium. During the growth period, the neuron progenitor cells proliferate. The progenitor cells differentiate in vivo, following implantation and can be induced to differentiate in vitro by addition of a differentiation agent; e.g., cyclic AMP.

DETAILED DESCRIPTION OF THE INVENTION

The present invention is based on the development of a method for isolating, culturing and proliferating neuron progenitor cells in vitro. The isolation and culture methods are designed to proliferate neuron progenitor cells in vitro to produce a culture having an increased number of neuron progenitor cells. Progenitor cells in the culture can differentiate to produce dopamine-producing cells in vitro, depending on the culture period and conditions, or can differentiate in vivo, following implantation.

In addition to increasing the number of neuronal cells through proliferation, the cultures can be frozen while substantially maintaining cell viability. When grown as aggregates, the progenitor cell cultures send out neurites which are not disrupted in the implantation process, thus maintaining a high percentage of viable cells upon implantation. Following implantation, a subpopulation of progenitor cells which did not differentiate in vitra differentiate in vivo and function as tyrosine hydroxylase-containing neurons, gaining the ability to produce functional effects about three to six months following implantation, depending on the species of the implanted tissue and of the host.

In addition to its use as an implant, a culture of this invention can be used for evaluating agents which inhibit or enhance neuroblast proliferation or differentiation or for evaluating the toxicity of an agent on neurons. Aggregate cultures are particularly advantages for these purposes. Methods for evaluation of pharmacological agents using cell cultures are well known and involve combining the agent with the culture and observing the effect of various concentrations of the agent on the cultured cells.

The process of this invention for preparing neuron progenitor cells comprises obtaining ventral mesencephalon tissue from a mammalian donor at the appropriate stage of embryonic development; dissociating of the tissue to obtain single cells and small cell clusters for culture; culturing the neuron progenitor cells in an initial culture medium which selects for a novel cell culture containing neuron progenitor cells and maintaining the culture for a period of time in a second medium during which the neuron progenitor cells proliferate.

As used herein, the following terms are defined as follows:

"Cell culture" or "tissue culture" refers to the maintenance of cell viability and function in vitra. It may or may not involve cell proliferation.

"Cell proliferation" is a process of cell multiplication by means of cell division. When this occurs in vitro to any significant level in monolayer cultures, it usually involves one or more subcultures.

"Subculture" means the transfer of cells from one culture vessel to another. The term is synonymous with the term "passage".

"Graft" is a cell culture which has been implanted into a host animal.

Key steps for culturing neuron progenitor cells are described in detail below. While the steps are provided in some detail, it will be readily apparent to a person skilled in the art that the procedures described can be modified and varied without departing from the objective thereof, and this invention is not limited to the specific details presented herein.

PREPARATION OF NEURON PROGENITOR CELL CULTURE

Embryonic mammalian tissue is used to prepare neuron progenitor cell cultures. The tissue can be from any mammalian source, conveniently from a large mammal. Preferably, the tissue is from a goat, cow, sheep or other commercially raised animal. Most preferred is the use of human or porcine tissue.

The donor embryo is in the early stages of development, prior to neurite formation. The tissue is removed from the dopaminergic system of the brain. Preferably, the tissue is from an area which differentiates to form an area of the brain with a relatively high concentration of TH-positive neurons. Most preferably, the tissue is from the ventral mesencephalon.

The objective of the tissue preparation procedure is to disperse the tissue into single cells and small aggregates (about 500 cells per aggregate) without prolonged exposure conditions that impair cell viability. A description of two tissue dissociation methods, mechanical and enzymatic, are described. Mechanical dissociation is preferred since the process is as effective as enzymatic digestion and avoids cell viability impairment caused by exposure to enzymes.

Also described is preparation of monolayer cultures and suspension (aggregate) cultures from the dissociated cells. Aggregate cultures are preferred for implantation, since the procedure allows neuron progenitor cell differentiation within the aggregates during the culture period without disruption of neurites during the implantation process. The aggregate size is controlled by the culture conditions. Preferably, culture conditions are used so that the size of the aggregates remains small enough to implant by injection through a catheter. Aggregate cultures conveniently range in size from about 100 to about 1000 microns.

The neuron progenitor cell culture aggregates have loci of undifferentiated cells and loci of neurons. The loci of undifferentiated cells may contain rosette-like structures in which mitotic figures are often seen. The loci of neurons contain TH-positive cell bodies whose neurites appear to extend to the periphery of the aggregates. Upon histological examination, the aggregates appear to be bordered by a layer of neuropil (an acellular, neurite-rich area).

Preparation of monolayer cultures is also described. Monolayer cultures may be advantageous for procedures in which selection of certain populations of cells is desired. The selected cells can be implanted or cultured as aggregates. Monolayers which will be implanted without intermediate culture as aggregates are preferably grown on a substrate which can be removed from the culture vessel and implanted, such as amniotic membranes, rather than a substrate where enzymatic digestion is required to remove the cell culture for implantation.

Gross examination of typical neuron progenitor cell "monolayer" cultures reveals interconnected three-dimensional structures, rather than the usual two-dimensional monolayer observed with most cell lines. It is thought that the proliferative capacity of these cells creates this three-dimensional effect. Over time, cells begin to migrate from these structures and form typical two-dimensional monolayers in which differentiating neurons and glia can be observed.

If desired, prior to implantation, neuron progenitor cell cultures can be successfully frozen and stored at the time of dissociation or following the completion of the selection period. The cultures can be induced to differentiate in vitro at any time.

In addition to being observably different from prior art neuron cell cultures, the neuron progenitor cell cultures of this invention are biochemically distinguishable from freshly prepared ventral mesencephalon cultures. In particular, for the same amount of embryonic tissue, a neuron progenitor cell culture of this invention produces approximately 100-fold the amount of catecholamines. Following in vitro differentiation, the cultures produce approximately ten-fold the amount of catecholamines of the non-differentiated cultures. In addition, the ratios of concentrations of the three major brain catecholamines (dopamine, epinephrine and norepinephrine) changes following differentiation.

Isolation of Tissue

Removal and Storage of Embryos
1. Remove embryos in amniotic sacs from uterus by sterile lavage with 0.15 M NaCl. Use embryos at Carnegie stages 15–18 for porcine or human tissue. (An explanation of the Carnegie stages can be found in "Developmental Stages in Human Embryos" by Ronan O'Rahilly and Fabiola Muller, Carnegie Institution of Washington (Carnegie Laboratories of Embryology, California Primate Research Center and Departments of Human Anatomy and Neurology; University of California, Davis) Publication 637, 1987 and "An Atlas for Staging Mammalian and Chick Embryos by H. Butler and B. H. Juurlink 1987, CRC Press, Inc.)
2. Store embryos in sterile "Transport Medium" (Jawamoto et al, *Brain Res.*, 384:84–93 [1986]—Formula: 54 mM $KH_2PO_4$, 30 mM $K_2HPO_4$, 195 mM D-sorbitol, 5 mM D-glucose, 20 mM sodium lactate, 50 μg/ml gentamicin) at 4° C. for up to 72 hours before proceeding with the cell preparation. That article is incorporated herein by reference in its entirety.
3. All subsequent procedures are performed aseptically.

Dissection of Embryos
1. Remove embryos from amniotic sac.
2. By fine dissection with forceps, peel back the skin from the head of the embryo to expose the meninges and the brain. At this time the fine curvatures of the brain surface and the numerous blood vessels on it will be apparent.
3. Make the first cut, a cross-section through the neural tube, immediately posterior to the isthmus separating the mesencephalon from the metencephalon.

4. Make cuts number 2 and number 3, which separate the dorsal region of the mesencephalon from the ventral region, and discard the dorsal segments.
5. Make cut number 4, at 90° from cut number 1, a cross-section through the neural tube anterior to the mesencephalon, releasing the ventral mesencephalon (VM). Tease away any membranes that are still attached.
6. An ideal VM section should be opaque, white in color, very soft in texture, and shaped roughly like a butterfly. Any trace of clear or semi-clear tissue (i.e. meninges) should be removed from the VM section.
7. Pool dissected VM pieces in a small drop of Hanks Basal Salt Solution (HBSS) (per liter: 0.14 g $CaCl_2$; 0.06 g $KH_2PO_4$; 0.4 g KCl; 0.1 g $MgCl_2.6H_2O$; 0.1 g $MgSO_4.7H_2O$; 8.00 g NaCl; 0.35 g $NaHCO_3$; 0.09 g $Na_2HPO_4.7H_2O$; 1.0 g D-glucose; 0.01 g phenol red) containing 50 μg/ml gentamicin and 50 mM Hepes buffer, pH 7.2 (Hanks/Hepes/gentamicin, hereinafter HHG). Keep pieces on ice in a small petri dish.

For human tissue, the dissection is essentially the same, but will first require a three-dimensional "reconstruction" of the tissue if it is not intact in order to visualize and identify the region of the mesencephalic flexure.

Following isolation of the tissue, the tissue is dissociated into single cells and small aggregates of cells (less than about 500 cells per aggregate). The dissociation can be by enzymatic or mechanical methods, or a combination thereof. Exemplary enzymatic and mechanical methods are described below. Following dissociation of the cells, the cells are cultured as monolayers or, preferably, in suspension cultures in which the cells form aggregates (aggregate cultures). Each cell culture type is described using a different dissociation procedure. However, any dissociation procedure can be used to prepare monolayer or aggregate cultures.

Aggregate cultures are seeded by placing a small number of cells in a small volume of medium, preferably 1.0 ml or less, more preferably less than 0.5 ml. Not more than about $10^5$ cells, preferably fewer than $10^4$ cells are seeded per culture. In a most preferred embodiment, from about $2.5 \times 10^3$ to about $5 \times 10^3$ cells per well are seeded in each well of a 48 well plate. Using seeding conditions that control the initial number of cells per culture tends to control the eventual size of the aggregates. In addition, use of smaller initial seeding concentrations produced smaller aggregates and enhanced the viability of the aggregates. Specifically, the absence of necrotic cells in the centers of the aggregates correlated with lower initial plating densities and maintaining smaller aggregate size.

In the culture process of this invention, the cultures are initially grown in a first culture medium which promotes the survival of neuron progenitor cells which are capable of proliferating in a serum-free, defined medium. The initial culture medium can be a basal medium supplemented with serum, hormones, growth factors and trace elements. Alternatively, the initial culture medium can be a basal medium supplemented with fetal cord serum, preferably from the same species as the cultured cells. Ham's F12 with 5% fetal cord serum is an effective initial culture medium. Preferably, the initial culture medium is Ham's F12 with Chang's supplement C (hereinafter Chang's) or a medium having a similar composition. Changes is preferably present at about 5% (v/v) or more. In a most preferred embodiment, the initial culture medium additionally contains glutamine at a concentration of about 2 mM and superoxide dismutase at about 100 U/ml. The cultures remain in the initial culture medium for at least 4.5 days prior to culture in growth medium. The growth medium is preferably added by day 7, but more preferably between days 4.5 to 5.5.

Mechanical Dissociation of Cells

Preparation of Aggregate Culture

1. The tissue is dissected as described above.
2. Collect tissue sections in a small (about 50 μl) drop of HHG in a small petri dish on ice.
3. Pool all sections in 1 drop of HHG, and chop into pieces 0.5 mm or smaller. Keep this on ice.
4. Remove the cap from a 50 ml centrifuge tube, place a 7×7 cm autoclaved 210 μmesh Nitex screen (Tetko cat. no. 3-210/36) over the opening and secure it in place with an autoclaved rubber band.
5. Repeat step 4 with a second centrifuge tube using a 130 μmesh Nitex screen (Tetko cat. no. 3-130/43).
6. Place 10 ml room temperature HBSS in a 15 ml centrifuge tube that had been rinsed with 4% bovine serum albumin (BSA) in HBSS (hereinafter HBSS/BSA) to form a BSA-coated tube. Add 0.1 ml of DNase stock. (DNase stock is Sigma cat. no. D4527 DNase at 1 mg/ml in HBSS.)
7. Place the tip of a sterile pasteur pipet into the flame of a burner so that melting of the tip closes the opening. Then heat the pipet at about 0.5 cm above the melted tip so that a hook is formed. Coat this pipet by dipping the hooked tip in HBSS/BSA.
8. Using an unaltered, BSA-coated pasteur pipet, transfer the tissue fragments onto the center of the 210 μNitex screen. Wash the tissue with about 2 ml of HHG, then remove as much liquid as possible from the screen with the pipet. Combine this liquid with the HBSS/DNase solution.
9. Using the curve on the hooked Pasteur pipet and a gentle scraping movement, work the tissue through the screen quickly, but gently, to prevent the tissue from drying.
10. Wash the screen with the DNase stock solution. Keep the wetted area to a minimum on the center of the screen.
11. Repeat steps 9 and 10 until no more tissue fragment is visible on the screen, using not more ,than 6 ml of the DNase stock solution.
12. Remove all liquid from the 210μscreen. Then carefully remove the rubber band and the screen.
13. Transfer the cell suspension to the center of the 130 μscreen using the unaltered BSA-coated pipet. Then repeat steps 9 through 12, using the remainder of the DNase stock solution.
14. Transfer the cell suspension from the tube with the 130 μscreen to the BSA-coated 15 ml tube (now empty of DNase stock solution). Then centrifuge at 150×g for 3 minutes.
15. Discard supernatant. Resuspend cells in suitable volume of an appropriate medium, preferably the initial culture medium. In general, 0.5–1.0 ml of F12+5% Chang's supplement C+2 mM glutamine+100 U/ml Superoxide Dismutase is an appropriate volume of a most preferred initial culture medium. (Chang's supplement C is commercially available from Irvine Scientific; Irvine, Calif.).

16. Remove 10 μl of cell suspension after gentle trituration. Add this to 40 μl of 0.04% Crystal Violet solution, then triturate with a micropipeter until a single nuclear suspension is obtained (about 100×). Count using a hemacytometer.

17. Gently triturate the cells before diluting to appropriate volume for seeding. Usually seeding is done at $3 \times 10^3$ cells in 0.3 ml in each well of a 48 well plate.

18. Various volumes of medium can be added 2 hours later to control aggregate formation. In particular, a volume of 0.45 ml yields single aggregates in each well of a 48 well plate. Volumes greater than 0.30 ml but less than 0.35 ml yield multiple aggregates in each well. These volumes were determined at 270 rpm on a mini-orbital shaker (Bellco; Vineland, N.J.). A speed of 180 rpm will yield single aggregates at various volumes. Sylgard 184 (Dow Corning Corp.; Midland, Mich.) coating of the wells may be necessary to inhibit aggregate adhesion to the well (particularly for human tissue ).

Switch medium to HN2 Medium 5 days later by removing about half of the medium and adding that volume of HN2 medium. Then feed about twice a week with HN2 Medium by removing approximately half of the medium and replacing that volume with fresh medium. Alternatively, the initial medium can be exchanged for HN2 medium at 5 days and half or all of the medium replaced for subsequent feedings. HN2 medium is a modified version of N2 medium (Bottenstein and Sato, PNAS 76:514–517 [1979]) which contains 1:1 v/v Dulbecco's Modified Eagle Medium (Dulbecco et al., Virology 8:396 [1959]):Ham's F12 (Ham, PNAS 53:288 [1965]). Those articles are incorporated herein by reference in their entirety. The formulae for each of the components of HN2 are shown below. HN2 Medium contains DMEM (low glucose):F12 1:1 v/v and the additional ingredients shown in Table 1. The formulae for DMEM and F12 are found in Tables 2 and 3, respectively.

TABLE 1

| HN2 Medium DMEM (low glucose): F12 1:1 v/v | |
|---|---|
| COMPONENT | CONCENTRATION |
| N2 medium | |
| insulin | 5 μg/ml |
| transferrin | 100 μg/ml |
| putrescine | 100 μM |
| selenium | 30 nM |
| progesterone | 20 nM |
| additional components | |
| glutamine | 2 mM |
| KCl | 25 mM |
| human serum albumin | 0.1% (g/100 ml) |

TABLE 2

| DULBECCO'S MODIFIED EAGLE MEDIUM[1] Low Glucose | |
|---|---|
| COMPONENT | mg/L |
| Inorganic salts: | |
| $CaCl_2$ (anhyd.) | 200.00 |
| $Fe(NO_3)_3 \cdot 9H_2O$ | 0.10 |
| KCl | 400.00 |
| $MgSO_4 \cdot 7H_2O$ | 200.00 |
| NaCl | 6400.00 |
| $NaHCO_3$ | 3700.00 |

TABLE 2-continued

| DULBECCO'S MODIFIED EAGLE MEDIUM[1] Low Glucose | |
|---|---|
| COMPONENT | mg/L |
| $NaH_2PO_4 \cdot H_2O$ | 125.00[2] |
| Other components: | |
| D-Glucose | 1000.00 |
| Phenol red | 15.00 |
| Sodium pyruvate | 110.00 |
| Amino Acids: | |
| L-Arginine HCl | 84.00 |
| L-Cystine | 48.00 |
| L-Glutamine | 584.00 |
| Glycine | 30.00 |
| L-Histidine $HCl \cdot H_2O$ | 42.00 |
| L-Isoleucine | 105.00 |
| L-Leucine | 105.00 |
| L-Lysine HCl | 146.00 |
| L-Methionine | 30.00 |
| L-Phenylalanine | 66.00 |
| L-Serine | 42.00 |
| L-Threonine | 95.00 |
| L-Tryptophan | 16.00 |
| L-Tyrosine | 72.00 |
| L-Valine | 94.00 |
| Vitamins: | |
| D-Ca pantothenate | 4.00 |
| Choline chloride | 4.00 |
| Folic acid | 4.00 |
| i-Inositol | 7.20 |
| Nicotinamide | 4.00 |
| Pyridoxal HCl | 4.00 |
| Riboflavin | 0.40 |
| Thiamine HCl | 4.00 |

[1]Dulbecco et al., Virology 8:396 (1959); Smith et al., Virology 12:185-196 (1960); Tissue Culture Standards Committee (TCSC), In Vitro 6(2):93 (1970).
[2]Value shown is in conformance with the TCSC, In Vitro, 9, No. 6 (1970).

TABLE 3

| F12 MEDIUM | |
|---|---|
| COMPONENT | mg/L |
| Inorganic salts: | |
| $CaCl_2 \cdot 2H_2O$ | 44.00 |
| $CuSO_4 \cdot 5H_2O$ | 0.00249 |
| $FeSO_4 \cdot 7H_2O$ | 0.834 |
| KCl | 223.60 |
| $MgCl_2 \cdot 6H_2O$ | 122.00 |
| NaCl | 7599.00 |
| $NaHCO_3$ | 1176.00 |
| $Na_2HPO_4 \cdot 7H_2O$ | 268.00 |
| $ZnSO_4 \cdot 7H_2O$[1] | 0.863 |
| Other components: | |
| D-Glucose | 1802.00 |
| Hypoxanthine | 4.10 |
| Linoleic acid | 0.084 |
| Lipoic acid | 0.21 |
| Phenol red | 1.20 |
| Putrescine 2HCl | 0.161 |
| Sodium pyruvate | 110.00 |
| Thymidine | 0.73 |
| Amino Acids: | |
| L-Alanine | 8.90 |
| L-Arginine HCl | 211.00 |
| L-Asparagine $\cdot H_2O$[1] | 15.01 |
| L-Aspartic acid | 13.30 |
| L-Cysteine $HCl \cdot H_2O$ | 35.12 |
| L-Glutamic acid | 14.70 |
| L-Glutamine | 146.00 |
| Glycine | 7.50 |
| L-Histidine $HCl \cdot H_2O$ | 20.96 |
| L-Isoleucine | 3.94 |
| L-Leucine | 13.10 |
| L-Lysine HCl | 36.50 |
| L-Methionine | 4.48 |
| L-Phenylalanine | 4.96 |
| L-Proline | 34.50 |
| L-Serine | 10.50 |
| L-Threonine | 11.90 |
| L-Tryptophan | 2.04 |

TABLE 3-continued

F12 MEDIUM

| COMPONENT | mg/L |
| --- | --- |
| L-Tyrosine | 5.40 |
| L-Valine | 11.70 |
| Vitamins: | |
| Biotin | 0.0073 |
| D-Ca Pantothenate[1] | 0.4800 |
| Choline chloride | 13.9600 |
| Folic acid | 1.300 |
| i-Inositol | 18.000 |
| Niacinamide | 0.0370 |
| Pyridoxine HCl | 0.0620 |
| Riboflavin | 0.0380 |
| Thiamine HCl | 0.3400 |
| Vitamin $B_{12}$ | 1.3600 |

[1]Value established by the TCSC.

HN2 medium is prepared in polycarbonate tubes and filter sterilized using Milex yellow (i.e. "protein" non-absorbing) filters (Millipore Corp., Bedford, MA). The medium is stored not more than 2 days at 4° C. prior to use.

Enzymatic Dissociation of Cells

Preparation of Monolayer Culture

1. Pool all dissected sections in a drop of HBSS. Chop into pieces not greater than about 0.5 mm with small razor blade holder.
2. Transfer pieces to a 15 ml tube previously rinsed with 4 ml of HBSS/BSA, using a Pasteur pipet previously washed with HBSS/BSA.
3. Centrifuge cells at 75×g for 2 minutes.
4. Resuspend the pellet in a minimum of 0.5 ml Dispase (Collaborative Research cat. no. 40235). This is sufficient volume for less than 5 embryos (as starting material). For 10 embryos, use 1 ml, etc.
5. Incubate 20 minutes at 37° C. with gentle shaking every 5 minutes to resuspend pieces.
6. Add 2 ml HBSS/BSA for every 0.5 ml Dispase.
7. Centrifuge cells at 75×g for 2 minutes.
8. Aspirate supernatant and discard.
9. Resuspend pellet in 0.9 ml HBSS+0.1 ml DNase stock solution. Gently triturate with a BSA-coated, fire-polished Pasteur pipet (bore reduced to about half of its normal diameter) until a homogeneous solution is obtained. Do not leave the cells in the DNase stock solution for more than 5 minutes.
10. Layer cell suspension over 4 ml of HBSS/BSA.
11. Centrifuge at 119×g for 15 minutes.
12. Aspirate the supernatant and discard. Resuspend the cell pellet in culture medium with the BSA-coated, fire-polished Pasteur pipet.
13. Count cells with a hemacytometer.
14. Before proceeding with cells triturate again with BSA-coated Pasteur pipet as cells clump rapidly upon standing.

Seeding Neural Epithelial Cells for Monolayer Cultures

1. Resuspend isolated cells at $5 \times 10^5$ cells/ml in F12 medium (Gibco cat. no. 320-1765) containing 5% v/v Chang's Supplement C (Irvine Scientific), and 2 mM glutamine (hereinafter F12+5% Chang's). 2. Seed cells on poly-l-ornithine coated (see below) tissue culture plastic at $0.85 \times 10^5$ cells/cm². Poly-l-ornithine coated plastic:

Prepare plastic the day prior to use. Dilute stock poly-l-ornithine (1.0 mg/ml poly-l-ornithine, Sigma P-2533 in sterile 0.2M borate buffer, pH 8) 1:250 v/v in sterile borate buffer. Add an appropriate volume to surface to be coated and incubate 4 hours at 37° C. Transfer plates to 4° C. for overnight storage. Aspirate poly-l-ornithine off the plate and rinse three times with sterile $H_2O$ before use.

3. The day after seeding cells, add an appropriate volume of fresh F12+5% Chang's to the cultures. On day 5 after seeding and every 3 to 4 days thereafter exchange feed, i.e., remove half of the "old" medium and replace with fresh HN2 Medium. When switching the initial culture medium to the growth medium, either all of the medium can be replaced or, preferably, half of the medium can be replaced with new HN2 Medium being used at each subsequent feeding.

Passaging Neural Epithelial Cells

1. Depending on growth, subculture prior to extensive neurite formation.
2. Pool media from wells or plates. Wash each well or plate containing attached cells one time gently with calcium-free, magnesium-free Hanks Basal Salt Solution (CMF-HBSS) and add to above medium.
3. Centrifuge 75×g for 2 minutes at room temperature. Resuspend the pellet in 0.5 ml 0.02% ethylenediamine tetraacetic acid (EDTA), 0.05% trypsin in CMF-HBSS (trypsin-EDTA). Incubate 37° C. for 5 minutes.
4. To washed, attached cells, add an appropriate volume of trypsin-EDTA. When passaging primary and secondary cultures, incubate at 37° C. for 10 to 15 minutes. For later passages, incubate only 5 minutes.
5. Pool trypsinates. Wash wells with F12+5% Chang's and add to trypsinate. Add F12+5% Chang's to equal the volume of the trypsinate.
6. Centrifuge at room temperature at 150×g for 2 minutes.
7. Resuspend the pellet in 0.75 ml HBSS and triturate with fine bore or very fine bore Pasteur pipet just until clumps disappear, usually not more than 20 times.
8. Add 0.75 ml F12+5% Chang's and layer on top of 4 ml of HBSS/BSA.
9. Centrifuge 119×g for 15 minutes.
10. Discard supernatant. Resuspend pellet in 0.75 ml F12+5% Chang's. Triturate ten times or so with very fine bore Pasteur pipet.
11. Count cells in a hemacytometer and resuspend in medium to $5 \times 10^5$ cells/ml. Plate on poly-l-ornithine coated plastic at $0.85 \times 10^5$ cell/cm².
12. Proceed as described for primary monolayer culture above or perform selection procedures, such as FACS (fluorescent-activated cell sorting) or magnetic bead antibody sorting, and reculture in monolayer as described above or reculture in aggregates as described. Following growth of the neuron progenitor cell cultures for 5-15 days, the cultures can be implanted. When convenient, the cultures can be stored frozen prior to implantation. A preferred procedure and thawing cells is described below.

Freezing and Thawing Neural Epithelial Cells The cultures can be frozen and thawed by the following procedure.

Freezing Cells

1. Cells from monolayer cultures are frozen by this procedure following the same procedure used for passaging cells. Aggregates are frozen in same medium, but need not be at any critical concentration of cells. They can be thawed back out as aggregates and recultured or transplanted.
2. Suspend cells in F12+5% Chang's+2 mM glutamine medium (at about $2 \times 10^7$/ml for trypsinates of monolayer cultures).
3. Cool on ice for about 5 minutes.
4. Add an equal volume of cold 20% dimethylsulfoxide (DMSO) in F12+5% Chang's dropwise while mixing for a final cell concentration of $10^7$/ml.
5. Incubate on ice for 30 minutes.
6. Aliquot into labeled, screw cap freezing vials. Label with cell type, passage number, date and volume frozen.
7. Transfer vials (wrapped in cotton) to a pre-cooled freezing carton at $-20°$ C. for 1 hour.
8. Transfer vials to a $-80°$ C. freezer overnight, then transfer to a liquid $N_2$-containing dewar flask.

Thawing Cells
1. Remove vials from liquid $N_2$.
2. Thaw rapidly in 37° C. water bath.
3. As soon as thawed (about 30 seconds for 150 μl), add an appropriate volume of F12+5% Chang's medium at 37° C. to obtain final cell concentration of $2 \times 10^6$ cells/ml. At this point cells may be transplanted or passaged further. A preferred transplantation procedure is described below. 4. For passaging monolayer cultures, plate cells on poly-l-ornithine-coated plastic at $3.4 \times 10^5$ cells/cm$^2$.

IN-VITRO DIFFERENTIATION OF PROGENITOR CELLS

Neuron progenitor cells can be induced to differentiate in vitro by adding a differentiation agent to the culture medium at an effective concentration for a time sufficient for progenitor cells in the culture to differentiate. A sufficient period of time can be determined by monitoring the cultures for a significant increase in levels of TH or dopamine.

Differentiation agents include sodium butyrate, butyric acid, cyclic adenosine monophosphate (cAMP) derivatives, phosphodiesterase inhibitors, adenylate cyclase activators and prostaglandins. Effective levels are determined empirically by titration. A preferred differentiation agent is a cAMP derivative. Preferred cAMP derivatives are 8-bromo-cyclic AMP and dibutyryl-cyclic AMP (dbc-AMP). Most preferred is dbc-AMP at a concentration in the range of from about 2 to about 5 mM (final concentration in the culture medium).

The differentiation agent can be added to the culture medium once the cells have been in growth medium for at least about five days. Preferably, the differentiation agent is added prior to ten days in growth medium.

When the growth medium is replaced during the differentiation period, the replacement medium contains the differentiation agent. Differentiation is substantially complete following at least about seven days of continuous exposure to the differentiation agent. Seven days of use of the differentiation agent is optimal. Following completion of differentiation, the differentiation agent is preferably removed. Prolonged exposure to the agent may be toxic. Following completion of differentiation, differetniated progenitor cells in the culture cease proliferation and are preferably transplanted.

When using the differentiated cells for implantation, the time required to cure Parkinsonian symptoms is shorter than when undifferentiated progenitor cell cultures are implanted. Differentiated cells do not require an initial period of time in vivo to differentiate to gain the ability to produce tyrosine hydroxylase.

TRANSPLANTING NEURAL EPITHELIAL CELLS

The neuron progenitor cell cultures can be transplanted by well known procedures for implantation of neural tissue. A preferred procedure is described below. Following transplantation, neuron progenitor cells in the resultant grafts differentiate to produce their differentiated counterparts, neurons. A subpopulation of the neurons are TH-containing neurons which produce functional effects in the host animal.

Preparation of Cells for Transplantation
1. Cells can be transplanted by this procedure:
   a. Immediately after isolation from the embryo;
   b. After passaging;
   c. After growth as an aggregate culture;
   d. After freezing and thawing; or
   e. After selection from a monolayer.
2. Resuspend cells at $1-5 \times 10^5$ cells/6 μof HBSS. Hold cells at 4° C. throughout the transplantation procedure.

Transplantation Procedure
1. Weigh and inject the rat with the Ketamine/Xylazine cocktail (Ketamine: Parke-Davis (Vetalar) Morris Plains, N.J.; Xylazine: Rugby (Gemini) Rockville Center, N.Y.) by intraperitoneal (IP) or intramuscular injections to induce surgical anesthesia. IP injections have a quicker onset of action and produce surgical anesthesia for approximately 30–45 minutes.
2. At 5–10 minutes post injection, check the rat for tail reflex. Absence of a tail pinch reflex is a fairly reliable indication that the rat has reached surgical anesthetic plane. Whisker movement and strong corneal reflex are indicators that a supplementary dose should be given (0.05–0.10 ml Ketamine/Xylazine). The cocktail tends to produce a characteristic "bugging" of the eyes.
3. Shave the animal at the site of incision.
4. Due to the length of surgical procedure, rinse the rates eyes with saline and place a drop of mineral oil in its eyes.
5. Position the rat in the ear bars of a Kopf stereotaxic apparatus by inserting one ear bar at a time into the auditory canal. Check the coordinate position of the incisor bar and then position it under the incisor teeth of the rat and pull taut. Close the nose clamp firmly but gently.
6. Make a 0.5" incision from eye midline to just above the ears. Cut the fascia in a crisscross pattern with the surgical knife and scrape the fascia away with a scalpel. Attach the hemostats to the remaining muscle and fascia at the borders of the incision to help reveal the skull surface. 70% alcohol-soaked applicators help to define the sutures. Bregma, lambda and sagittal sutures should be visible if the incision was made correctly.
7. Draw up 6 μl of cell suspension into a 10 μl Hamilton syringe fitted with a 22 gauge, 1" long, blunt-end needle.
8. Mount the syringe in the syringe holder. Align the needle over the bregma suture. Coordinates relate to anatomical positions within the rat brain, as taken from a stereotaxic atlas. All numbers read on the stereotaxic apparatus. When needle is at bregma (the zero position in the anterior-posterior (AP) and medial-lateral (ML) directions) and skull surface (the Dorsal-Ventral (DV) zero coordinate), these are the zero coordinates. (In calculating the zero coordinate position, it may be necessary to take an average zero coordinate if a poor intersection coronal and sagittal of the sutures exist.) The transplant coordinates are added and/or subtracted from the zero settings. Moving to these coordinates will put the needle into the anatomical area of the brain that corresponds to the transplant coordinates taken from the atlas.

Calculate the surgical structure coordinates desired for the AP, ML positions. Again, lower the needle tip to the surface of the skull but this time at the needle entry site. Record the DV zero coordinates and then calculate the structure depth. Coordinates for transplant: AP+1.0, ML 2.5, DV 6.2 and 4.5 from skull surface, with incisor bar at zero.

9. Mark the location of entry with a ball-point pen. Clear the needle and syringe out of the way by turning the DV knob in a counter clockwise direction and then drill a hole in the skull using a hand-driven pin vise and bit. Be careful to only drill through the skull and not through the dural membrane.

10. Lower the syringe to lowest of DV coordinates.

11. Inject 3 µl of cells at each site, at a rate of 1 µl/min. Wait 2 minutes before raising needle to second site. Wait another 2 minutes before removing needle at a rate of 1 mm/min. Removal rate can be increased to 2 mm/min. for the last couple of millimeters.

12. Remove the rat from the stereotaxic device. Swab any clotted blood, apply wound powder, suture and reapply wound powder on the closed wound (Nitro-fur-wound powder; Life Science Products; St. Joseph, Mo.).

This invention is further illustrated by the following specific, but non-limiting examples. Unless otherwise specified, all temperatures are in degrees centigrade and all percentages are in weight percents. Procedures which have been reduced to practice are presented in the past tense, and procedures and products which are first reduced to practice in the filing of this application are presented in the present tense.

EXAMPLE 1

Fixation of Brain

Rat brain tissue was fixed by the following procedure.

1. The rat is deeply anesthetized with pentobarbital.
2. Set the pump on 45 (about 30 ml/min) and prime the tube with 0.1M phosphate buffered saline (hereinafter PBS or 0.1M PBS) (Formula: 14.8 g NaH$_2$PO$_4$, 4.3 g Na$_2$HPO$_4$, 7.2 g NaCl for 1 L. of 0.1M PBS).
3. Open the thoracic cavity, clamp off the descending aorta and insert the needle into the left ventricle. Cut a small hole in the right atrium and start the pump.
4. Perfuse 100-200 ml of PBS, turn off the pump, transfer the tube to the 4% paraformaldehyde without creating air bubbles, and restart the pump. Perfuse approximately 250 ml. Turn the pump off, disengage the needle, rapidly decapitate the rat, and dissect out the brain.
5. Place the brain in 4% paraformaldehyde (4% paraformaldehyde in 0.1M PBS) for 2 hours. Wash in PBS and transfer to 30% sucrose with 0.1% sodium azide overnight and hold no longer than 1 week for sectioning.

EXAMPLE 2

Sectioning of Fixed Brain Tissue

Brain tissue which was fixed according to the procedure in Example 1 was sectioned by the following procedure.

1. Cut into blocks about 7 mm thick.
2. Snap freeze blocks in dry ice/ethanol.
3. Cut frozen blocks on a sliding microtome at 40µ.
4. Store sections at 4° C. in 0.1M PBS with 0.1% Na azide up to 2 weeks before staining for tyrosine hydroxylase (TH). For long term storage: 30% ethylene glycol, 25% glycerin in 0.05M phosphate buffer.

EXAMPLE 3

Tyrosine Hydroxylase Staining of Sections

Sections prepared according to the procedure described in Example 2 were stained for tyrosine hydroxylase by the procedure described below.

Day 1

1. Wash sections in 0.1M PBS pH 7.4, two times, 5 minutes each.
2. Incubate in 3% hydrogen peroxide in distilled water for 5 minutes to block endogenous peroxidase activity.
3. Wash briefly in distilled water.
4. Wash in PBS three times, 5 minutes each.
5. Incubate in PBS with 3% goat serum (normal goat serum, Vector Labs; Burlingame, Calif.) for 30 minutes (to block non-specific staining when using a primary rabbit antibody and a secondary goat anti-rabbit antibody).
6. Wash in PBS three times, 5 minutes each.
7. Incubate in tyrosine hydroxylase antibody (Eugene Tech International; Allendale, N.J. at 1:500 dilution or East Acres; Southbridge, Mass. at 1:2000 dilution for rat brains and 1:2500 dilution for mouse brains) diluted in PBS with 1% goat serum and 0.1% Triton X-100 overnight at room temperature, agitated on a fish-tank aerator.

Day 2

8. Wash in PBS with 1% goat serum three times, 5 minutes each.
9. Incubate in Biotinylated anti-Rabbit IgG (Vector, Burlingame, Calif. reconstituted in 1 ml, use 1:300 dilution in PBS) for 1 hour.
10. Wash in PBS with 1% goat serum three times, 5 minutes each.
11. Incubate in ABC solution (Vector, Burlingame, Calif. dilute each solution A and B 1:100 in PBS, then let sit for 30 minutes before incubation) for 1 hour.
12. Wash in PBS three times, 5 minutes each.
13. Incubate in 3,3 diaminobenzidene (DAB) substrate (Litton Bionetics, Durham, N.C.; reconstitute in 1 ml 0.01M phosphate buffer (PB) [use 0.1M phosphate buffer diluted 1:10], then dilute DAB 1:10 with 0.01M PB, filter and add 2 μl/ml of 30% Hydrogen Peroxide) for 10 minutes.
14. Wash in tap water.
15. Mount the floating sections from PBS on subbed slides, (slides dipped in 0.25% chromium potassium sulfate and 2.5% gelatin in distilled water, then dried) dry, wash in distilled water, dehydrate in 95% EtOH 2 minutes, 100% EtOH two times, 2 minutes each, then Hemo-De (Xylene substitute, Fisher Corporation, Springfield, N.J.) three times, 2 minutes each, and coverslip using Protexx mounting media (VWR, San Francisco, Calif.).

EXAMPLE 4

Quantitative Analysis of TH-Positive Cell Bodies in Sections from Grafted Brains Tyrosine hydroxylase (TH) positive staining was used as a marker for those neurons which contain dopamine. TH-positive cell bodies in the graft area which had been stained by the procedure described in Example 3 were quantitated by the procedure described below.

1. All TH-positive cell bodies are counted in every third section throughout the graft using a Zeiss microscope at 100 × magnification.
2. The section thickness is measured at 1000× using an oil immersion objective. Thickness in microns is found by focusing on the top of the section, recording the micrometer reading on the focusing knob of the microscope, and then focusing through the section to the bottom and computing the difference in readings. The thickness is measured in two different areas on five representative sections.
3. The cell body length is measured at 1000 × magnification using an ocular micrometer or the video image analyzer. Ten typical cell body lengths are measured per section on ten representative sections. Due to shrinkage in the section thickness and cell diameter during histological preparation, these measurements must be taken at the time of counting.
4. Approximation of the number of cells in the sections not counted is done using the formula being:

$$A_1 = A + [(B-A)/3] \text{ and } A_2 = A + 2[(B-A)/3]$$

where: A = the number of cells counted in the first section, and B = the number of cells counted in the second section, and $A_1$ and $A_2$ are the number of cells from the sections not counted between A and B.
5. Abercrombie correction for double counting cell in adjacent sections was used to correct the approximation. The formula is:
corrected number = (experimental cell number). [(average section thickness) / (average cell diameter + average section thickness)]

EXAMPLE 5

Implantation of Progenitor Cell Cultures In Vivo

Grafts of cultured fetal pig progenitor cell cultures of this invention function in the Parkinsonian rat model. (The Parkinsonian rat model was described by Strecker et al., *Exp. Brain Res.* 76:315-322 [1989] and Brundin et al., *Neurosci. Lett.* 61:79-84 [1985]. Those articles are incorporated herein by reference in their entirety.) Donor tissue was dissected from the ventral mesencephalon of stage 15-18 fetal pigs (21-24 day fetal pigs), enzymatically dissociated, mechanically triturated, and cultured as described above for aggregate cultures for 15 days. Typically, $3 \times 10^4$ cells were plated per well; and, after 6-150× proliferation, the cells were transplanted (1 well/rat). The cultured tissue was injected directly into the dopamine-denervated striata of host rats. By 16 weeks post-implantation, eleven of 20 grafted rats have shown behavioral recovery in the amphetamine-induced rotation test. Histological analysis revealed very large grafts containing numerous dopamine neurons as identified by tyrosine hydroxylase (TH) immunohistochemistry according to the procedure described in Examples 1-4.

The average density of the TH-positive neurons in functioning grafts was found to be greater than 100 cells/mm³. Most commonly, TH-positive neurons were found to be situated at the graft periphery. Occasionally, rosette-like structures were observed within the grafts.

A parallel experiment combining immunohistochemistry and autoradiography has shown that when such cultures are labeled for 2 days in vitro with 3H-TdR (days 5-7) and grafted at day 7, numerous TH-positive grafted neurons containing label are found at 4 weeks post-grafting. That experiment is described in Example 6.

EXAMPLE 6

Proliferation of Progenitor Cell Cultures In Vitro

1. Donor tissue was dissected from the ventral mesencephalon of stage 16 fetal pigs, enzymatically dissociated, and cultured as described for aggregate cultures for 7 days.
2. From day 5 to day 7, the cells were labelled with tritiated thymidine, at 0.1 μCi/ml (New England Nuclear, 20 Ci/mM, 1 mCi/ml, Boston, Mass.)
3. On day 7, medium was removed, cells were washed three times with HBSS, and transplanted as described into nude mice.
4. Brains were sectioned as described after 4-and 8-week transplant times.
5. Sections were stained for TH as described.
6. Slides were prepared for autoradiography: slides were dipped into NTB2 (1:1 with H₂O) (all reagents: Kodak, Rochester, N.Y.), and air dried in the dark.
7. Slides were exposed at 4° C. for 2 weeks.
8. Slides were warmed to room temperature, and developed in 50% Dektol for 1 minute.
9. Slides were rinsed in H₂O for 10 seconds.
10. Slides were fixed in 25% Kodafix for 4 minutes.
11. Slides were rinsed in H₂O for 10 minutes before drying and coverslipping.
12. TH(+) cells were counted, and the percentage of those cells which had incorporated label into their nuclei was determined.
13. 50% of all TH(+) cells had incorporated thymidine between days 5 and 7 in culture.

EXAMPLE 7

Minimum TH(+) Cell Density Required For Cure

1. Twenty-seven ablated rats were transplanted with stage 15-18 porcine tissue (day 21 to 24), either fresh or aggregated in culture, by techniques described.

2. The rats were analyzed for function by the procedure described in Strecker et al., Exp. Brain Res. 76:315-322 (1989) during a 16-week period post-implantation.
3. The total number of TH(+) cells in each graft was counted as described.
4. The area of the graft in each section was calculated with the use of Vidometric 150 software (American Innovision, San Diego, Calif.).
5. The total volume of each graft was calculated using the same formula used for determining the total number of TH(+) cells in the graft, as described.
6. The number of TH(+) cells/mm$^3$ was determined for each graft.
7. The results indicated that for 100% functional recovery at least 100 TH(+) cells must be present in each mm$^3$ of tissue.
8. Comparison of the group of transplants which showed 100% functional recovery to the group of transplants which showed either partial or no functional recovery by a Mann-Whitney test showed that the densities of the 2 groups are significantly different ($p<0.0005$).

EXAMPLE 8

In Vitro Induction of Differentiation

Eight replicate aggregate cultures of human neuron progenitor cells prepared as described above were switched from initial medium to growth medium on day 5. On day 14, the following concentrations of potential differentiation agents, retinoic acid and di-butyryl cyclic AMP (dbc-AMP) were added to the cultures.

Retinoic acid ($\times 10^{-7}$M): 0; 0.2; 1.0; 5.0
dbc-AMP (mM): 0; 0.4; 2.0; 10.0

Following seven days in the presence of the differentiation agent, the cultures were evaluated for the amount of tyrosine hydroxylase (TH) DNA by standard protein immuno-slot-blot techniques. The cultures without differentiation agent were used as controls. All of the cultures with added retinoic acid had from about 80 to 110% of the amount of TH as the control cultures. For the cultures with dbc-AMP, the amount of TH production was significantly increased as shown below.

| dbc-AMP (mM) | 0.4 | 2.0 | 10.0 |
|---|---|---|---|
| % of control DNA | 400 | 650 | 175 |

The study demonstrates that the amount of TH DNA in the cultures was significantly increased using dbc-AMP, but was unchanged using retinoic acid.

Six replicate samples of two porcine cultures from two different litters (designated 1133-44 and 1016-94) were switched to growth medium at day 5 and grown for 10 days in the absence of a differentiation agent followed by 7 days in the presence of the concentrations of dbc-AMP stated below. The amount of TH/DNA was evaluated by slot-blot as described above. The results are illustrated below.

| dbc-AMP (mM) | % of Control Culture | |
|---|---|---|
| | 1133-44 | 1016-94 |
| 0 | 100 | 100 |
| 0.5 | 125 | 140 |
| 1.0 | 130 | 160 |
| 2.0 | 175 | 260 |
| 5.0 | 275 | 330 |
| 10.0 | 200 | 200 |

As shown in the table, the most effective concentration range for dbc-AMP as a differentiation agent is from 2.0 to 5.0 mM.

EXAMPLE 9

Analysis of Catecholamines of Neuron Progenitor Cell Cultures

The catecholamine content of neuron progenitor cell cultures was studied to characterize changes in catecholamine production following in vitro induction of differentiation. An HPLC analysis determined the approximate concentration and ratios of the three major brain catecholamines; dopamine, epinephrine and norepinephrine.

The cell cultures analyzed included a "control" culture. The control culture was freshly isolated cells from ten porcine embryos (21-day ventral mesencephalon) prepared as described in Example 5. The "standard" culture was a neuron progenitor cell culture of this invention prepared as described in Example 5 from the same embryo preparation as the control culture and cultured for two weeks. That culture included approximately one embryo-equivalent of cells. The third culture was a two week progenitor cell culture prepared as the standard culture and then differentiated using 5 mM dibutyryl cyclic AMP for one additional week as described in Example 8 (for a total of three weeks in culture). That culture included approximately one-third embryo-equivalents of cells.

The HPLC analysis determined that the freshly prepared culture did not have detectable amounts of catecholamines. (The HPLC method can detect the presence of 10 picograms of catecholamines.) The standard culture had at least about 100 picograms of catecholamines (at least 100× the catecholamine content per embryo equivalent of freshly isolated cells). The differentiated culture had several fold greater catecholamine content (at least 3×) than the standard culture (at least 10× the catecholamine content per embryo equivalent of the standard culture).

In addition to producing substantially more catecholamines than the standard culture, the differentiated neuron progenitor cell culture produced different proportions of the three major brain catecholamines. The ratio of the concentration of dopamine to epinephrine to norepinephrine for the standard culture and the differentiated culture are shown below.

| | dopamine | epinephrine | norepinephrine |
|---|---|---|---|
| standard | 1.00 | 0.85 | 0.49 |
| differentiated | 1.00 | 0.99 | 0.63 |

This Example demonstrates that the cultures of this invention are biochemically distinguishable from freshly isolated ventral mesencephalon cells from which they were derived. The Example also demonstrates that in addition to the observable differences in the cell cultures following differentiation which are described in Example 8, the cultures also produce more catecholamines having a different ratio of the major brain catecholamines.

What is claimed is:

1. A culture consisting essentially of mammalian ventral mesencephalon neuron progenitor cells or mammalian ventral mesencephalon neuron progenitor cells and their differentiated counterparts, said neuron progenitor cells being taken from a region of the brain that produces dopaminergic cells at a stage of development when the region of the brain has no dopamine-containing cells, said neuron progenitor cells in said culture having undergone at least one round of cell division after dissociation of tissue used to establish said culture, said progenitor cells in said culture being capable of seven to eight rounds of cell division after dissociation of said tissue.

2. The culture of claim 1 wherein said progenitor cells are porcine.

3. The culture of claim 1 wherein said progenitor cells are human.

4. The culture of claim 1 wherein said culture is capable of curing Parkinsonian symptoms about 4 months following implantation.

5. The culture of claim 1 wherein said culture comprises cell aggregates.

6. The culture of claim 5 wherein said aggregates range in size from about 100 to about 1000 microns.

7. The culture of claim 5 wherein said aggregates have loci of undifferentiated cells and loci of neurons.

8. A method for evaluating an agent which inhibits or enhances neuroblast proliferation or differentiation or for evaluating the toxicity of an agent on neurons comprising combining said agent with a culture of claim 1.

9. A method for producing a culture comprising neuron progenitor cells comprising:
  a. obtaining ventral mesencephalon tissue from a mammalian embryo at Carnegie stages from 15 through 18;
  b. dissociation of said tissue to obtain single cells and small cell clusters for culture;
  c. culturing said single cells and small cell clusters in an initial culture medium which promotes the survival of neuron progenitor cells which are capable of proliferating in serum-free, defined medium for a sufficient period of time to produce a cell culture containing neuron progenitor cells capable of proliferating in serum-free, defined medium; and
  d. growing said cell culture containing neuron progenitor cells in a medium which maintains neuronal cells.

10. The method of claim 9 wherein said medium of step (c) is Ham's F12 medium supplemented with Chang's supplement C.

11. The method of claim 10 wherein said medium is additionally supplemented with glutamine and superoxide dismutase.

12. The method of claim 9 wherein said medium of step (d) is HN2 medium.

13. The method of claim 16 wherein said medium of step (d) is HN2 medium.

14. The method of claim 9 wherein said period of time is 5 days.

15. The method of claim 9 wherein said culture is an aggregate culture.

16. The method of claim 14 wherein not more than $10^5$ cells are seeded per culture.

* * * * *

UNITED STATES PATENT AND TRADEMARK OFFICE
CERTIFICATE OF CORRECTION

PATENT NO.   :   5,411,883
DATED        :   May 2, 1995
INVENTORS    :   Barbara D. Boss and Dennis H. Spector It is certified that error appears in the above-identified patent and that said Letters Patent is hereby corrected as shown below:

Column 22, line 27, delete "HN2" and insert --N2--

Column 22, line 28, delete "16" and insert --12--

Signed and Sealed this

Twelfth Day of December, 1995

Attest:

BRUCE LEHMAN

*Attesting Officer*     Commissioner of Patents and Trademarks